US008685074B2

(12) United States Patent
Eidenschink et al.

(10) Patent No.: US 8,685,074 B2
(45) Date of Patent: Apr. 1, 2014

(54) BALLOON CATHETER

(75) Inventors: Tracee Eidenschink, Wayzata, MN (US); Richard Olson, Blaine, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2158 days.

(21) Appl. No.: 11/282,252

(22) Filed: Nov. 18, 2005

(65) Prior Publication Data

US 2007/0118169 A1 May 24, 2007

(51) Int. Cl.
*A61M 29/00* (2006.01)

(52) U.S. Cl.
USPC .......................................... 623/1.11; 606/194

(58) Field of Classification Search
USPC .................. 623/1.11; 606/191, 192, 194, 198
See application file for complete search history.

(56) References Cited

U.S. PATENT DOCUMENTS

| | | | |
|---|---|---|---|
| 4,276,874 A | 7/1981 | Wolvek et al. .................. 120/1 |
| 4,444,186 A * | 4/1984 | Wolvek et al. ................ 606/194 |
| 4,646,719 A * | 3/1987 | Neuman et al. ................. 600/18 |
| 4,813,934 A * | 3/1989 | Engelson et al. ........... 604/99.02 |
| 5,078,727 A | 1/1992 | Hannam et al. ............... 606/194 |
| 5,087,246 A | 2/1992 | Smith ............................. 604/96 |
| 5,370,615 A | 12/1994 | Johnson ......................... 604/96 |
| 5,405,380 A | 4/1995 | Gianotti et al. ................... 623/1 |
| 5,423,755 A | 6/1995 | Kesten et al. .................. 604/96 |
| 5,512,051 A | 4/1996 | Wang et al. .................... 604/96 |
| 5,573,520 A | 11/1996 | Schwartz et al. .............. 684/282 |
| 5,599,326 A * | 2/1997 | Carter ........................... 604/524 |
| 5,752,935 A | 5/1998 | Robinson et al. ............... 604/97 |
| 5,820,613 A | 10/1998 | Van Werven-Franssen et al. ............................. 604/282 |
| 5,855,565 A | 1/1999 | Bar-Cohen et al. ........... 604/104 |
| 6,117,296 A | 9/2000 | Thomson ....................... 204/607 |
| 6,129,737 A | 10/2000 | Hamilton et al. ............. 606/194 |
| 6,249,076 B1 | 6/2001 | Madden et al. ............... 310/363 |
| 6,388,043 B1 | 5/2002 | Langer et al. ................... 528/80 |

(Continued)

FOREIGN PATENT DOCUMENTS

EP 0619749 10/1994
EP 1 120 129 8/2001

(Continued)

OTHER PUBLICATIONS

D. Zhou et al., "Actuators for the Cochlear Implant," *Synthetic Metals* 135-136 (2003) 39-40.

(Continued)

*Primary Examiner* — Thomas McEvoy
*Assistant Examiner* — Julie A Szpira
(74) *Attorney, Agent, or Firm* — Vidas, Arrett & Steinkraus, P.A.

(57) ABSTRACT

A catheter system comprises a catheter, an inner shaft, an expandable balloon, and an elongate advancement member. The expandable balloon has an unwrapped state and rewrapped state and the advancement member has a first state and a second state. When the advancement member is in the first state the expandable balloon is in the unwrapped state, and when the advancement member is in the second state the expandable balloon is in the rewrapped state. The unwrapped state has a first length and a first diameter, the rewrapped state has a second length and a second diameter, the second length is equal to or greater than the first length, and the second diameter is less than first diameter. The advancement member in the second state extends through the interior region defined by the expandable balloon.

18 Claims, 4 Drawing Sheets

(56) References Cited

U.S. PATENT DOCUMENTS

| | | | |
|---|---|---|---|
| 6,514,237 B1 * | 2/2003 | Maseda | 604/533 |
| 6,515,077 B1 | 2/2003 | Su et al. | 310/332 |
| 6,545,391 B1 | 4/2003 | Su et al. | 310/332 |
| 6,664,718 B2 | 12/2003 | Pelrine et al. | 310/800 |
| 6,679,836 B2 | 1/2004 | Couvillon, Jr. | 600/146 |
| 6,749,556 B2 | 6/2004 | Banik | 600/30 |
| 6,770,027 B2 | 8/2004 | Banik et al. | 600/146 |
| 6,812,624 B1 | 11/2004 | Pei et al. | 310/800 |
| 6,835,173 B2 | 12/2004 | Couvillon, Jr. | 600/146 |
| 6,911,764 B2 | 6/2005 | Pelrine et al. | 310/328 |
| 6,921,360 B2 | 7/2005 | Banik | 600/30 |
| 6,940,211 B2 | 9/2005 | Pelrine et al. | 310/330 |
| 6,969,395 B2 | 11/2005 | Eskuri | 606/200 |
| 6,982,514 B1 | 1/2006 | Lu et al. | 310/300 |
| 6,997,870 B2 | 2/2006 | Couvillon, Jr. | 600/146 |
| 2003/0068522 A1 | 4/2003 | Wang | 428/654 |
| 2003/0236445 A1 | 12/2003 | Couvillon, Jr. | 600/114 |
| 2004/0068161 A1 | 4/2004 | Couvillon, Jr. | 600/143 |
| 2004/0087982 A1 | 5/2004 | Eskuri | 606/153 |
| 2004/0143160 A1 | 7/2004 | Couvillon, Jr. | 600/114 |
| 2004/0225318 A1 | 11/2004 | Eidenschink et al. | 606/194 |
| 2004/0236366 A1 | 11/2004 | Kennedy, II et al. | 606/192 |
| 2005/0004425 A1 | 1/2005 | Banik | 600/30 |
| 2005/0085693 A1 | 4/2005 | Belson et al. | 600/146 |
| 2005/0102017 A1 * | 5/2005 | Mattison | 623/1.11 |
| 2005/0107669 A1 | 5/2005 | Couvillon, Jr. | 600/146 |
| 2005/0165439 A1 | 7/2005 | Weber et al. | 606/191 |
| 2005/0177130 A1 | 8/2005 | Konstantino et al. | 604/509 |
| 2006/0041264 A1 | 2/2006 | Eskuri | 606/153 |
| 2006/0111618 A1 | 5/2006 | Couvillon, Jr. | 600/152 |

FOREIGN PATENT DOCUMENTS

| | | |
|---|---|---|
| JP | 63-192457 | 8/1988 |
| JP | 2-119875 | 5/1990 |
| WO | WO 98/50101 | 11/1998 |

OTHER PUBLICATIONS

E.W.H. Jager, E. Smela, O. Inganas, "Microfabricating Conjugated Polymer Actuators," *Science*, 290, 1540-1545, 2000.

E. Smela, M. Kallenbach, and J. Holdenried, "Electrochemically Driven Polypyrrole Bilayers for Moving and Positioning Bulk Micromachined Silicon Plates," *J. Microelectromechanical Systems*, 8(4), 373-383, 1999.

*Proceedings of the SPIE*, vol. 4329 (2001) entitled "Smart Structures and Materials" 2001. see Madden et al., "Polypyrrole actuators: modeling and performance," pp. 73-83.

U.S. Appl. No. 11/280,120, filed Nov. 16, 2005, Weber et al.
U.S. Appl. No. 11/368,927, filed Mar. 6, 2006, Kornkven Volk et al.
U.S. Appl. No. 11/411,360, filed Apr. 25, 2006, Kornkven Volk et al.
U.S. Appl. No. 11/496,248, filed Jul. 31, 2006, Eidenschink et al.

* cited by examiner

BALLOON CATHETER

CROSS-REFERENCE TO RELATED APPLICATIONS

Not Applicable

STATEMENT REGARDING FEDERALLY SPONSORED RESEARCH

Not Applicable

FIELD OF THE INVENTION

In some embodiments this invention relates to implantable medical devices, their manufacture, and methods of use. Some embodiments are directed to delivery systems, such as catheter systems of all types, which are utilized in the delivery of such devices.

BACKGROUND OF THE INVENTION

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents and similar devices such as stent, stent-grafts, expandable frameworks, and similar implantable medical devices, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

In some situations pertinent to this art, a problem associated with stent delivery is the removal of the stent delivery system itself once the stent has been implanted within a body lumen. The problem relates to the inadequate "rewrap" of the balloon around the catheter. If a balloon does not adequately deflate and rewrap around the catheter after stent delivery, the balloon profile may be large enough to inhibit proper removal of the catheter following stent delivery.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In order to place the stent, inflation fluid is injected into the balloon so as to cause balloon expansion. During balloon expansion, the balloon, which had been wrapped about the catheter via folds in the balloon, is stretched significantly. After the stent has been placed in situ, the inflation fluid is removed from the catheter. The deflated balloon, however, rarely returns to its pre-inflated size. Instead, the deflated balloon has stretched such that the extra "slack" resulting from the balloon's stretching during the inflation procedure prevents tightly rewrapping the balloon about the catheter shaft. A tightly rewrapped balloon is important because it reduces the overall profile of the catheter, which allows for easier withdrawal of the catheter from the body. In the invention, the slack is removed from the deflated balloon when an advancement member applies tension to the balloon. As the slack is removed, the balloon's profile will decrease and it will twist, rewrapping itself about the catheter shaft along the previous folds, thereby returning substantially to its pre-inflation wrapped state. Existing balloon designs that promote rewrapping are described in U.S. Pat. Nos. 5,512,051 and 6,129,737, each of which is incorporated herein by reference in their entirety.

In at least one embodiment, the invention is directed to a catheter system with a balloon expandable stent. The catheter system may be used to deploy a stent within a body lumen.

In at least one embodiment, the catheter system comprises an outer shaft, an inner shaft, an expandable balloon, and an elongate advancement member. The expandable balloon has an unwrapped state and a rewrapped state and the advancement member has a first state and a second state. The advancement member is in the first state when its distal end is not applying tension to the expandable balloon; the advancement member is in the second state when its distal end is applying tension to the expandable balloon. When the advancement member is in the first state, the expandable balloon is in the unwrapped state, and after the advancement member is in the second state, the expandable balloon becomes the rewrapped state. The unwrapped state has a first length and a first diameter and the rewrapped state has a second length and a second diameter, the second length being equal to or greater than the first length and the second diameter being less than the first diameter. The advancement member in the second state extends through the interior region defined by the expandable balloon.

In some embodiments, the distal end region of the outer shaft sealingly engages the proximal end region of the expandable balloon and the distal end region of the expandable balloon sealingly engages the inner shaft. The distal end region of the advancement member biases the distal end region of the expandable balloon when the advancement member is in the second state.

In at least one embodiment, the outer shaft defines an inflation lumen. The inflation lumen is in fluid communication with the proximal end region of the expandable balloon, and the expandable balloon is capable of receiving an inflation fluid delivered through the inflation lumen. In some embodiments the proximal end region of the outer shaft is engaged to a handle, or manifold. In at least one embodiment the proximal end region of the advancement member is engaged to a manifold. The advancement member manifold and the inflation member manifold may be moved relative to each other.

In some embodiments, the distal end region of the advancement member is constructed of material that is stiffer in a longitudinal direction than the material of the proximal end region of the advancement member.

In at least one embodiment, the distal end region of the outer shaft engages the proximal end region of the expandable balloon. Furthermore, at least a portion of the distal end region of the advancement member comprises at least one individual member. The distal end region of the expandable balloon engages at least a portion of the distal end region of the advancement member. Also, the distal end region of the expandable balloon can be sealed to a portion of the advancement member.

In some embodiments, the at least one individual member extends along a longitudinal axis of the catheter, the at least one individual member being wound about the longitudinal axis in a spiral when the advancement member is in the first state. When the advancement member is in the second state, the at least one individual member is substantially parallel to the longitudinal axis. At least a portion of the advancement member has a length greater in the second state than in the first state.

In at least one embodiment, the advancement member comprises an electroactive polymer having an unexpanded state and an expanded state, the volumetric size of the electroactive polymer being greater in the expanded state than in the unexpanded state. The advancement member is in the first state when the electroactive polymer is in the unexpanded state and the advancement member is in the second state when the electroactive polymer is in the expanded state.

The invention also contemplates embodiments of methods of rewrapping an expanded balloon. In some embodiments, the method of rewrapping an expandable balloon of a catheter system comprises the first step of extracting substantially all inflation fluid from an expanded balloon disposed about a catheter, the catheter comprising an outer shaft, an inner shaft, the expanded balloon, and an elongate advancement member. Next, tension is applied to the balloon along a longitudinal axis, thereby increasing the length of the balloon and reducing the diameter of the balloon.

In at least one embodiment, the method of rewrapping an expandable balloon of a catheter system further includes advancing the advancement member until the distal end region of the advancement member biases the distal end of the expandable balloon. Then, the advancement member manifold is interlocked with the inflation member manifold, thereby maintaining tension on the balloon.

In some embodiments, the step of applying tension to the expandable balloon further comprises the step of applying a voltage across a first electrode and a second electrode, each of the first electrode and the second electrode in electric communication with an electroactive polymer, thereby expanding the electroactive polymer from an unexpanded state to an expanded state, the electroactive polymer having a volumetric size greater in the expanded state than in the unexpanded state.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
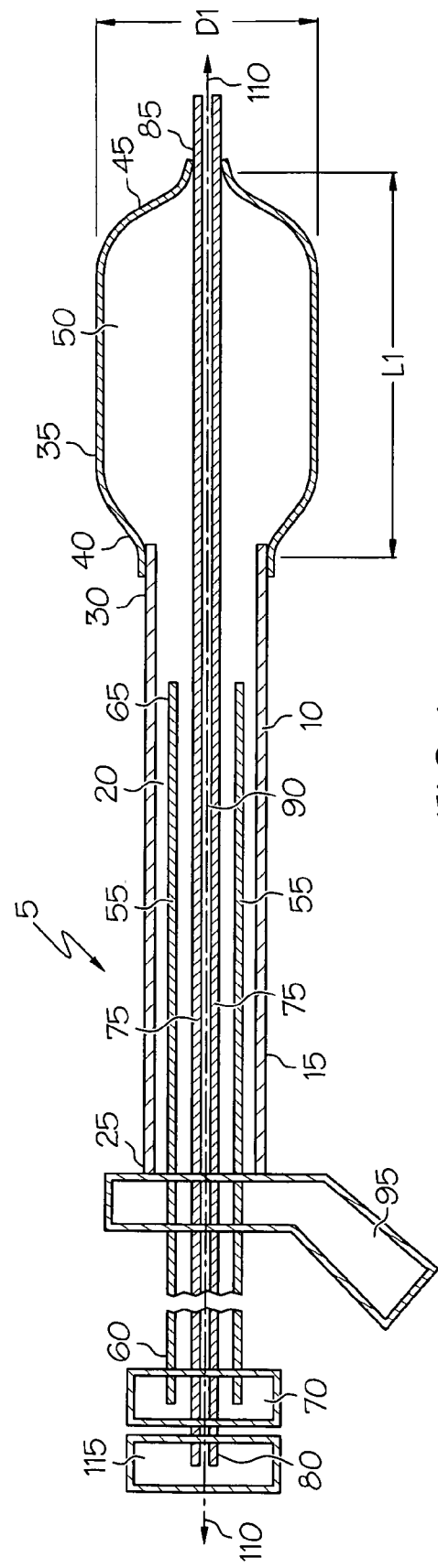
FIG. 1 is a longitudinal cross-sectional side view of an embodiment of the invention, comprising an expandable balloon in an unwrapped state.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Depicted in the figures are various aspects of the invention. Elements depicted in one figure may be combined with, and/or substituted for, elements depicted in another figure as desired.

Referring now to the drawings, FIG. 1 illustrates a catheter system, shown generally at 5, comprising a catheter 10, outer shaft 15, and expandable balloon 35. Outer shaft 15, having proximal end region 25 and distal end region 30, defines an inflation lumen 20 through which an inflation fluid (not shown) can inflate expandable balloon 35. The inflation fluid is delivered via inflation member manifold 95 which is engaged to the proximal end region 25 of outer shaft 15. Expandable balloon 35, shown in an unwrapped state, is disposed about outer shaft distal end region 30. Expandable balloon 35 defines an interior region 50 through which inflation lumen 20 extends, first through expandable balloon proximal end region 40 and then through expandable balloon distal end region 45. In the unwrapped state, expandable balloon 35 has a length L1 and diameter D1. The proximal end region 40 of expandable balloon 35 is securingly engaged to the distal end region 30 of outer shaft 10; distal end region 45 of expandable balloon 35 is securingly engaged to inner shaft 90.

Catheter system 5 further comprises an elongate advancement member 55 with a proximal end region 60 and distal end region 65. Outer shaft 15 is disposed about advancement member 55. Engaged to the proximal end region 60 of advancement member 55 is advancement member manifold 70. The distal end region 65 of advancement member 55, shown in FIG. 1 in its first state, does not bias the distal end region 45 of expandable balloon 35.

At least one embodiment of the invention contemplates using an advancement member 55 at least partially comprised of an electroactive polymer (EAP). An electroactive polymer refers to a polymer that acts as an insulating dielectric between two electrodes and may deflect upon application of a voltage difference between the two electrodes. Electroactive polymers (EAP) are materials such as polypyrrole, polyalanine, polyacetylene, polythiophene and polyvinylidene difluoride (PVDF), etc. that show shape deformation when an electric field is applied. Electroactive polymer materials can be manufactured such that when there is a voltage difference between the two electrodes, the EAP material increases in volumetric size. Alternatively, the EAP material can be manufactured such that when there is a voltage difference between the two electrodes, the material decreases in volumetric size. When an electric field is applied across the EAP, the EAP deforms as a result of stresses generated by the movement of water and mobile positive ions in the polymer.

Electroactive polymers are characterized by their ability to change shape in response to electrical stimulation. EAPs include electric EAPs and ionic EAPs. Piezoelectric materials may also be employed but tend to undergo small deformation when voltage is applied. Conductive plastics may also be employed.

Further information regarding EAP actuators may be found in Ser. No. 11/496,248, the entire content of which is incorporated by reference herein.

Additional information regarding EAP actuators, their design considerations, and the materials and components that may be employed therein, can be found, for example, in E. W. H. Jager, E. Smela, O. Inganäs, "Microfabricating Conjugated Polymer Actuators," *Science,* 290, 1540-1545, 2000; E. Smela, M. Kallenbach, and J. Holdenried, "Electrochemically Driven Polypyrrole Bilayers for Moving and Positioning Bulk Micromachined Silicon Plates," *J. Microelectromechanical Systems,* 8(4), 373-383, 1999; U.S. Pat. No. 6,249,076, assigned to Massachusetts Institute of Technology, and *Proceedings of the SPIE,* Vol. 4329 (2001) entitled "Smart Structures and Materials 2001: Electroactive Polymer and Actuator Devices (see, e.g., Madden et al, "Polypyrrole actuators: modeling and performance," at pp. 72-83), each of which is hereby incorporated by reference in its entirety.

Furthermore, networks of conductive polymers may also be employed. For example, it has been known to polymerize pyrrole in electroactive polymer networks such as poly(vinylchloride), poly(vinyl alcohol), NAFION®, a perfluorinated polymer that contains small proportions of sulfonic or carboxylic ionic functional groups, available from E.I. DuPont Co., Inc. of Wilmington, Del. Electroactive polymers are also discussed in detail in commonly assigned copending U.S. patent application Ser. No. 10/763,825, the entire content of which is incorporated by reference herein. Existing electroactive polymers are also described in U.S. Pat. No. 6,515,077, U.S. Pat. No. 6,545,391, and U.S. Pat. No. 6,664,718. Also, electroactive polymers used in conjunction with medical devices are described in U.S. Pat. No. 6,514,237, U.S. Pat. No. 5,855,565, U.S. Pat. No. 6,679,836, U.S. Published application No. 20050102017, U.S. Published application No. 20040143160, U.S. Published application No. 20040068161, and U.S. patent application Ser. No. 10/763,825. Existing catheter designs are described in U.S. Pat. No. 5,752,935 and E.P. 0619749.

As is known in the field of electroactive polymers, electrodes, connected to a voltage source, are attached to the EAP. By applying a voltage across the electrodes, the EAP material can be expanded, or activated, such that the volumetric size of the EAP increases, thereby lengthening advancement member 55. This invention contemplates that an advancement member 55 comprised of EAP could be positioned such that the distal end region 65 of the advancement member 55 biases distal end region 45 of expandable balloon 35, thereby lengthening expandable balloon 35, upon activation of the EAP material.

Catheter system 5 also includes an inner shaft 75 with proximal end region 80 and distal end region 85. Inner shaft 80 defines a guidewire lumen 90 through which a guidewire (not shown) can be threaded. Engaged to the proximal end region 80 of inner shaft 75 is guidewire manifold 115.

Figure 2:
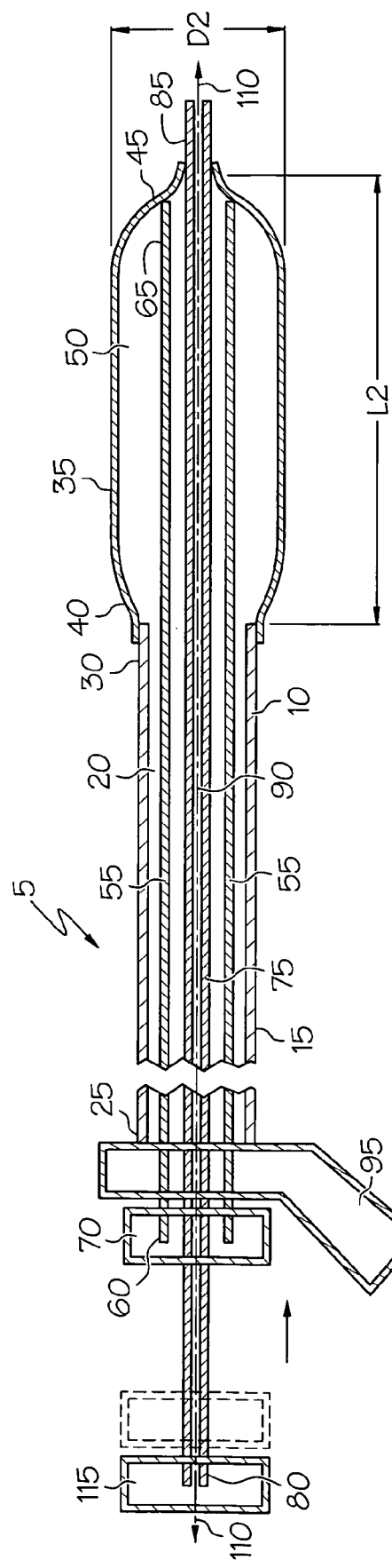
FIG. 2 is a longitudinal cross-sectional side view with partial cutaway of the embodiment shown in FIG. 1, wherein the expandable balloon is in a rewrapped state.

Referring now to FIG. 2, expandable balloon 35 is shown in a rewrapped state. In the rewrapped state, expandable balloon 35 has length L2 and diameter D2. Length L2 is greater than unwrapped state length L1 (shown in FIG. 1) and diameter D2 is less than unwrapped diameter D1 (shown in FIG. 1). Substantially all inflation fluid (not shown) used to expand expandable balloon 35 has been removed. Advancement member 55 is shown advanced along longitudinal axis 110 of catheter 10 such that distal end region 65 of advancement member 55 biases distal end region 45 of expandable balloon 35. Expandable balloon 35 is expanded further by advancement of advancement member 55 from a first state to a second state. Therefore, slack in the unexpanded balloon is removed as a result of the advancement member 55 biasing distal end region 45 of expandable balloon 35, thereby allowing improved rewrap. In a preferred embodiment, the distal end region 65 of advancement member 55 is constructed of a rigid material capable of extending expandable balloon 35. In some embodiments, the entire advancement member 55 is made of material that is stiff in a longitudinal direction, thus preventing, or at least minimizing, compression of the material in a longitudinal direction. There are a number of materials known in the art to be stiff in a longitudinal direction such as hypotube and PEEK™, for example. The material, however, is capable of flexing when bent at an angle relative to the longitudinal axis, thereby allowing the material to track through a tortuous body lumen. In some embodiments, the ability to flex may be the result of the material being patterned cut. Pattern cutting involves removing material from specific areas of a hypotube, for example, which allows the hypotube to flex more in the areas with less material. However, the invention contemplates using a material more rigid at the distal end region 65 of advancement member 55 than at the proximal end region 60, thereby allowing more flexibility of the advancement member 55 as the catheter 10 tracks through a body lumen. Tension may be maintained on expandable balloon 35 by interlocking advancement member manifold 70 with inflation member manifold 95. A number of common interlocking mechanisms, not shown, are available to sustain the tension on the expandable balloon, for example a standard LUER® lock connector.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments at least a portion of a deliverable stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

Figure 3:
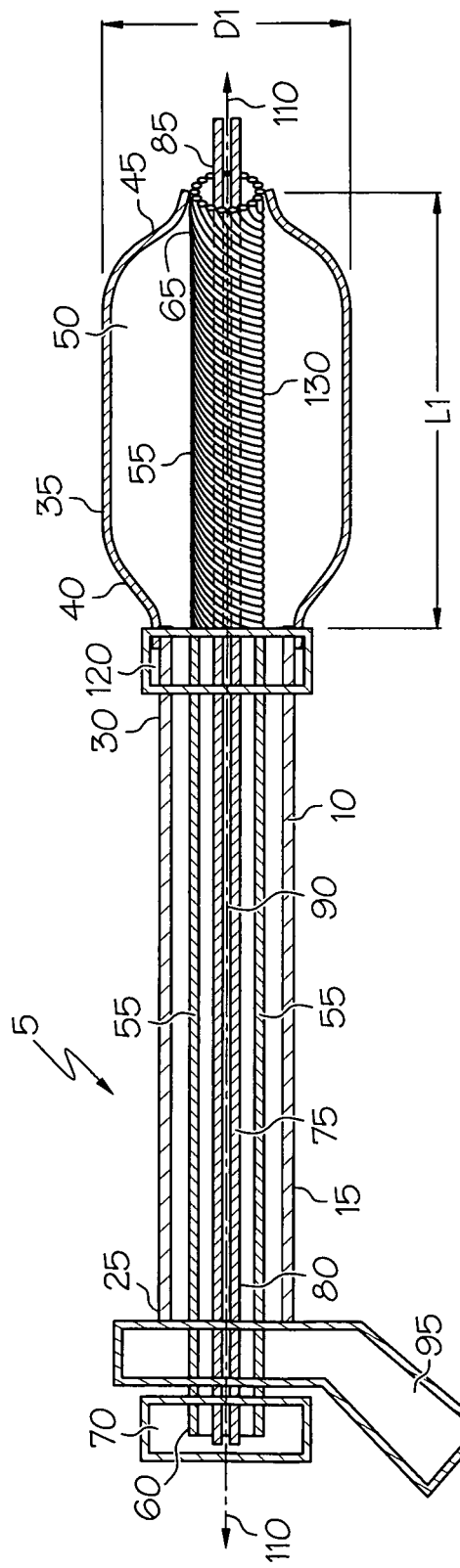
FIG. 3 is a longitudinal cross-sectional side view with partial cutaway of an embodiment of the invention, wherein the advancement member comprises a plurality of individual members, the individual members shown configured in a spiral around a longitudinal axis.

Referring now to FIG. 3, the invention also contemplates an advancement member 55, whose distal end region 65 is engaged to the distal end region 45 of expandable balloon 35, in contrast to the embodiment shown in FIG. 1. In the embodiment depicted in FIG. 3, collar 120 engages proximal end region 40 of expandable balloon 35 to distal end region 30 of outer shaft 15. Collar 120 reinforces the bond between the expandable balloon 35 and outer shaft 15. That is, collar 120 is provided to act as a stabilizing member so that neither the outer shaft 15 nor the balloon 35 rotate when a torquing force is applied to twist the advancement member. Distal end region 45 of expandable balloon 35 is engaged to the distal end region 65 of advancement member 55. Advancement member 55 is shown comprised of at least one individual member 130. In the embodiment shown in FIG. 3, the plurality of individual members 130 extends along the longitudinal axis 110 of catheter 10, and in the first state are wound about the longitudinal axis in a spiral, for example. It should be noted that the members 130 may also be wound in a helix. Or, each individual member 130 may be toroidal (i.e. doughnut-shaped) and aligned concentrically with other toroidal members 130. The proximal end region 60 of advancement member 55 is engaged to advancement member manifold 70 such that when sufficient torque is applied to advancement member manifold 70, rotation is produced in advancement member 55, particularly in individual members 130. Expandable balloon 35 of FIG. 3 is shown in an unwrapped state, with length L1 and diameter D1.

Figure 4:
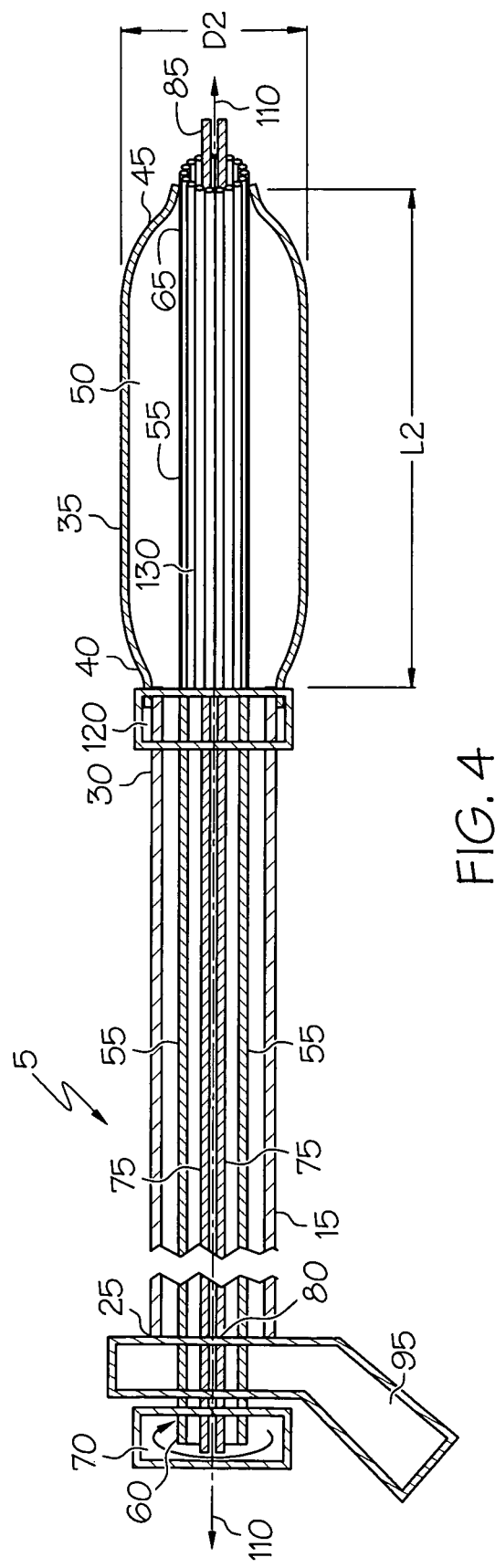
FIG. 4 is a longitudinal cross-sectional side view with partial cutaway of the embodiment shown in FIG. 3, wherein the advancement member has been torqued, thereby straightening the individual members and lengthening the expandable balloon.

In FIG. 4 in at least a portion of the distal end region 65 of advancement member 55, at least one individual member 130 extends along the longitudinal axis 130 of catheter 10. A plurality of individual members 130 are shown in FIG. 4 after torque is applied to advancement member manifold 70 in a direction opposite the direction the individual members were wound about the longitudinal axis 130. Individual members 130 therefore unwind after torque is applied to the advancement member manifold 70, and as a result, extend substantially parallel to longitudinal axis 130 of catheter 10. Because of the unwinding of individual members 130, at least a portion of the distal end region 65 of advancement member 55 lengthens, causing the length of expandable balloon 35 to extend to L2, a length greater than the length L1 of FIG. 3. Therefore, slack in the unexpanded balloon is removed as a result of the advancement member 55 biasing distal end region 45 of expandable balloon 35, thereby allowing improved rewrap. Furthermore, the diameter D1 of expandable balloon 35 in FIG. 3 decreases to diameter D2 due to the lengthening of advancement member 55. In some embodiments, the individual members 130 are wires. However, this invention contemplates using other suitable individual members 130 that are sufficiently malleable to be wound and unwound in the manner described above.

Furthermore, the invention also contemplates using EAP as the individual members 130. If using EAP, at least one embodiment contemplates not initially winding the individual members 130 about the longitudinal axis, as in FIG. 3. Rather, the individual members 130 comprised of EAP could begin in an unactivated state substantially parallel to the longitudinal axis 110 of catheter 10. Then, upon activation, the individual members 130 of EAP lengthen, thereby lengthening expandable balloon 35, like in the manner depicted in FIG. 4. In another embodiment, the individual members could be circumferential rings formed of EAP material such that activation of the EAP material would expand the rings, resulting in biasing of the balloon 35.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A catheter system comprising: a catheter, the catheter comprising an expandable balloon and an elongate advancement member, the expandable balloon defining an interior and having a diameter and a length, the expandable balloon further having an unwrapped state and a rewrapped state, in the unwrapped state the diameter being greater than in the rewrapped state, the length in the rewrapped state being at least as great as the length in the unwrapped state, the advancement member comprising a proximal end region and a distal end region, at least a portion of the distal end region of the advancement member extending through the interior of the expandable balloon, the at least a portion of the distal end region of the advancement member being engaged to a distal end region of the balloon, the advancement member having a first state and a second state, in the first state the at least a portion of the distal end region of the advancement member being spirally disposed about a longitudinal axis of the catheter, in the second state the at least a portion of the distal end region of the advancement member being substantially parallel to the longitudinal axis of the catheter, wherein when the advancement member is in the first state the expandable balloon is in the unwrapped state, and when the advancement member is in the second state the expandable balloon is in the rewrapped state.

2. The catheter system of claim 1, the catheter further comprising an outer shaft, a collar, an engagement region, a proximal end region of the expandable balloon engaged to a distal end region of the shaft at the engagement region, the collar extending around the engagement region.

3. The catheter system of claim 2 the catheter further comprising an inner shaft, wherein the inner shaft is disposed about the longitudinal axis of the catheter, the advancement member being disposed about the inner shaft.

4. The catheter system of claim 3 wherein the at least a portion of the distal end region of the advancement member comprises an individual member.

5. The catheter system of claim 3 wherein the at least a portion of the distal end region of the advancement member comprises a plurality of members.

6. The catheter system of claim 3, the advancement member further comprising an electroactive polymer having an unexpanded state and an expanded state, the volumetric size of the electroactive polymer being greater in the expanded state than in the unexpanded state, the advancement member being in the first state when the electroactive polymer is in the unexpanded state, the advancement member being in the second state when the electroactive polymer is in the expanded state.

7. The catheter system of claim 3, the inner shaft defining a guide wire lumen.

8. The catheter system of claim 1 the catheter further comprising:
an outer shaft having a proximal end region and a distal end region, the distal end region of the outer shaft engaged to the proximal end region of the expandable balloon; and
an inner shaft having a proximal end region and a distal end region, the distal end region of the inner shaft engaged to the distal end region of the expandable balloon, the at least a portion of the distal end region of the advancement member being spirally disposed about the inner shaft when the advancement member is in the first state, the at least a portion of the distal end region of the advancement member being substantially parallel to the longitudinal when the advancement member is in the second state.

9. The catheter system of claim 8, the inner shaft defining a guide wire lumen.

10. The catheter system of claim 8, at least a portion of the proximal end region of the advancement member being positioned within the outer shaft.

11. The catheter system of claim 8 further comprising:
an inflation lumen, the inflation lumen defined by the outer shaft, the inflation lumen being in fluid communication with the proximal end region of the expandable balloon, the expandable balloon capable of receiving an inflation fluid delivered through the inflation lumen;
an inflation member manifold engaged to the proximal end region of the outer shaft, the inflation member manifold in fluid communication with the inflation lumen; and
an advancement member manifold engaged to the proximal end region of the advancement member, wherein the advancement member manifold moves relative to the inflation member manifold.

12. The catheter system of claim 1, the proximal end region of the advancement member being distal to the expandable balloon.

13. A method of rewrapping an expanded balloon of a catheter system comprising the steps of:
extracting substantially all inflation fluid from an expanded balloon disposed about a catheter, the catheter comprising the expanded balloon, an advancement member manifold, an inflation manifold, and an elongate advancement member, the advancement member having a proximal end region and a distal end region and at least one individual member;
applying tension to the balloon along a longitudinal axis, thereby increasing the length of the balloon and reducing the diameter of the balloon;
advancing the advancement member until the distal end region of the advancement member biases the distal end of the expandable balloon; and
interlocking the advancement member manifold with the inflation member manifold, thereby maintaining tension on the balloon.

14. The method of claim 13, the advancement member having a first state wherein the at least one individual member is spirally disposed about the longitudinal axis and a second state wherein the at least one individual member is parallel to the longitudinal axis, the at least one individual member being in the second state when torque is applied to the proximal end region of the advancement member, the method further comprising the step of applying torque to the proximal end region of the advancement member thereby unwinding the at least one individual member and increasing the length of at least a portion of the distal end region of the advancement member.

15. The method of claim 13 the advancement member comprising an electroactive polymer, wherein the method further comprises the step of applying a voltage across a first electrode and a second electrode, each of the first electrode and the second electrode in electric communication with the electroactive polymer, thereby expanding the electroactive polymer from an unexpanded state to an expanded state, the electroactive polymer having a volumetric size greater in the expanded state than in the unexpanded state.

16. The method of claim 13, the catheter further comprising an outer shaft, the outer shaft defining an inflation lumen, the inflation member manifold in fluid communication with the inflation lumen, the inflation lumen in fluid communication with the balloon, the advancement member manifold engaged to the proximal end region of the advancement member, and the advancement member disposed within the inflation lumen.

17. The method of claim 16, the catheter further comprising an inner shaft, the inner shaft defining a lumen, the advancement member being disposed about the inner shaft.

18. The method of claim 14, the advancement member manifold being engaged to the proximal end region of the advancement member, wherein applying torque to the proximal end region of the advancement member comprises applying torque to the advancement member manifold.

* * * * *